United States Patent

Cunci et al.

[11] Patent Number: 5,752,969
[45] Date of Patent: May 19, 1998

[54] INSTRUMENT FOR THE SURGICAL TREATMENT OF AN INTERVERTEBRAL DISC BY THE ANTERIOR ROUTE

[75] Inventors: Olivier Cunci, Le Havre; Jacques Pierre Beurier, Saint Adresse, both of France

[73] Assignee: Sofamor S.N.C., Rang du Fliers, France

[21] Appl. No.: 578,557

[22] PCT Filed: Jun. 16, 1994

[86] PCT No.: PCT/FR94/00728

§ 371 Date: Jul. 18, 1996

§ 102(e) Date: Jul. 18, 1996

[87] PCT Pub. No.: WO95/00197

PCT Pub. Date: Jan. 5, 1995

[30] Foreign Application Priority Data

Jun. 17, 1993 [FR] France ................. 93 07330

[51] Int. Cl.[6] ........................................ A61B 17/32
[52] U.S. Cl. ............................... 606/167; 604/272
[58] Field of Search ........................ 604/272–274, 604/264; 606/185, 167, 170

[56] References Cited

U.S. PATENT DOCUMENTS

| | | | |
|---|---|---|---|
| 4,345,596 | 8/1982 | Young | 604/272 |
| 5,431,661 | 7/1995 | Koch | 604/272 |
| 5,484,442 | 1/1996 | Sloane, Jr. et al. | 604/272 |

FOREIGN PATENT DOCUMENTS

| | | |
|---|---|---|
| 0138 089 | 4/1985 | European Pat. Off. . |
| 0334 116 | 9/1989 | European Pat. Off. . |
| 3936811 A1 | 3/1989 | Netherlands . |
| WO 91/19528 | 12/1991 | WIPO . |
| WO 92/21298 | 12/1992 | WIPO . |

*Primary Examiner*—Michael Buiz
*Assistant Examiner*—Patrick W. Rasche
*Attorney, Agent, or Firm*—Woodard, Emhardt, Naughton, Moriarty & McNett

[57] ABSTRACT

An instrument including a guide needle (1), at least two nesting concentric tubes (2–6) placed over the guide needle, and an outer working tube (7) concentric with said tubes. The tip of the outer tube (7) is provided with a device (11) for spacing apart the bodies of vertebrae adjacent to the disk and keeping them apart during surgery, while its proximal end is provided with a hand grip (8). Anterior percutaneous nuclear incision performed with said instrument enables puncture of the disk, and particularly excision of the nucleus, to be performed easily, more quickly and more effectively than with the conventional posterolateral approach, while avoiding any damage to the anatomical environment of the patient.

9 Claims, 3 Drawing Sheets

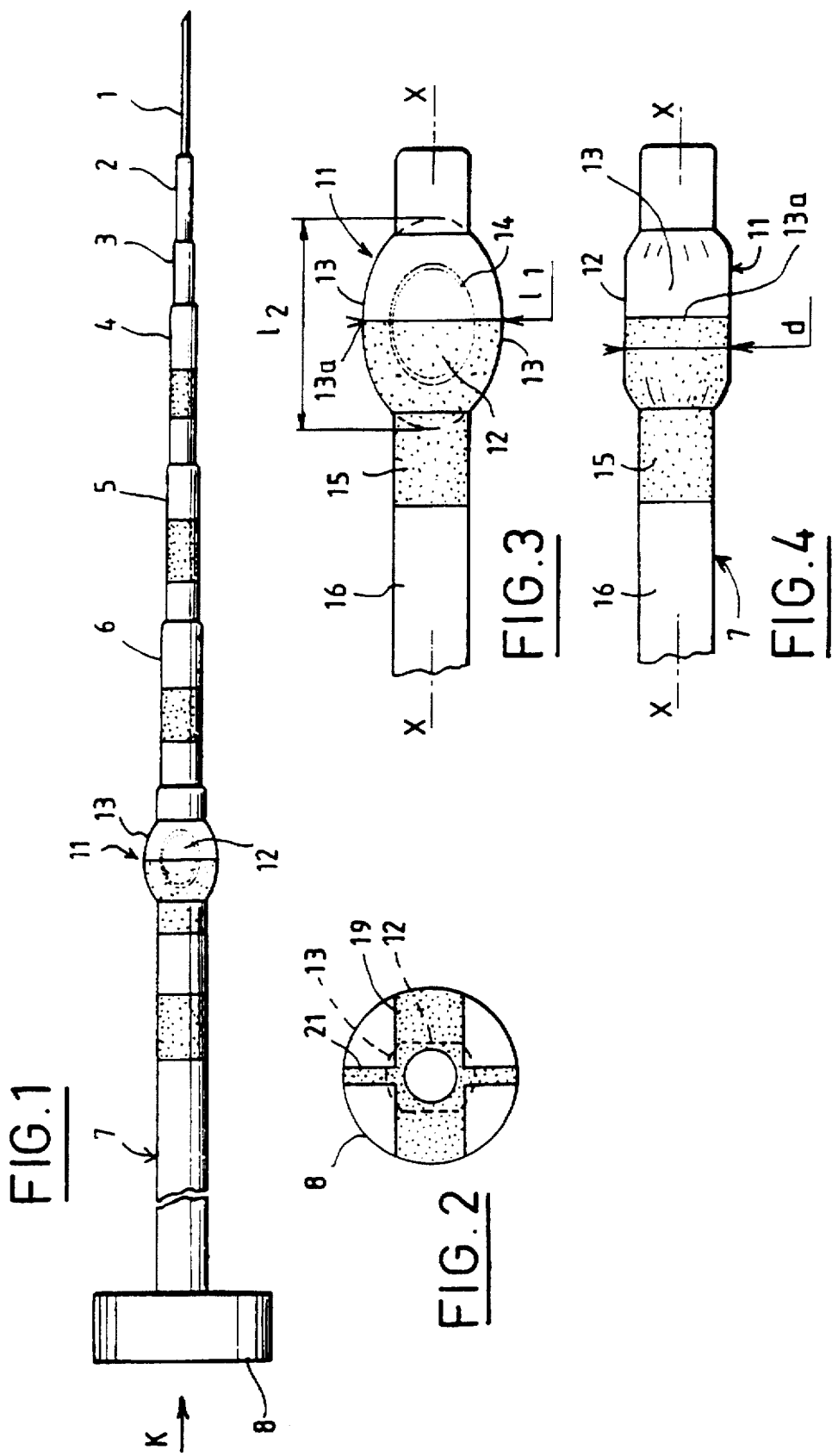

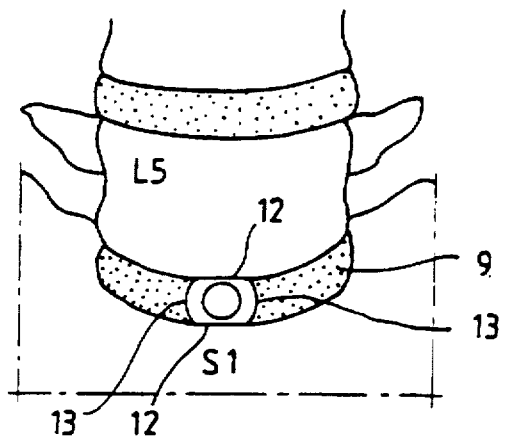
FIG.6
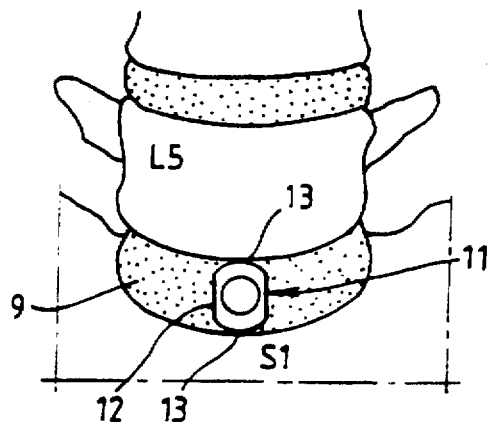
FIG.7
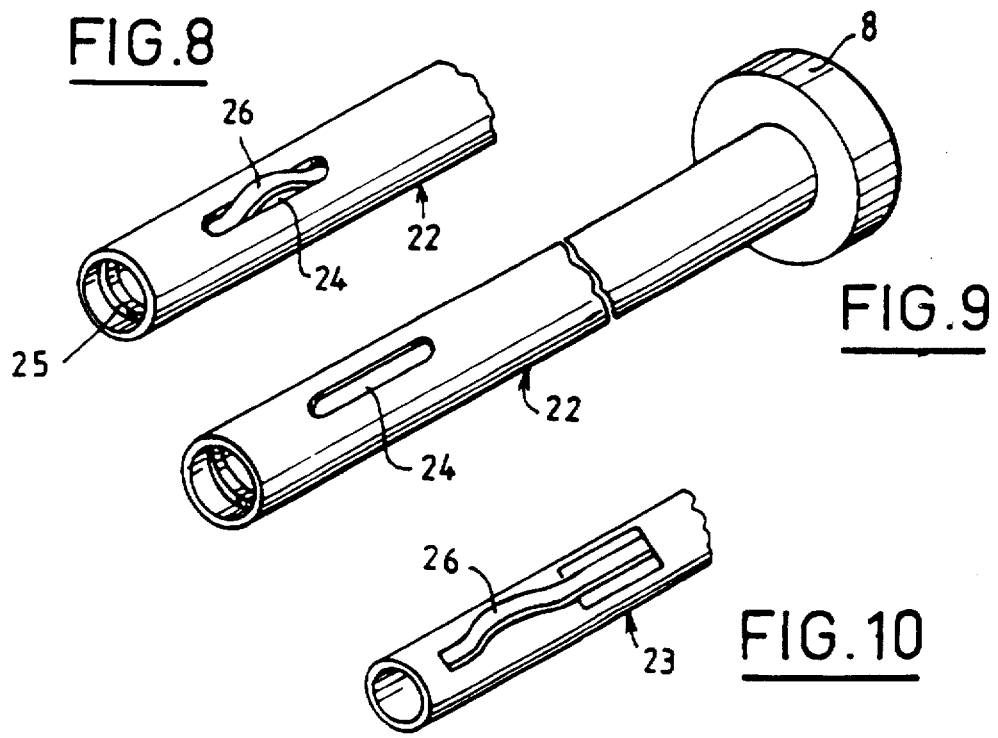
FIG.8
FIG.9
FIG.10

INSTRUMENT FOR THE SURGICAL TREATMENT OF AN INTERVERTEBRAL DISC BY THE ANTERIOR ROUTE

The present invention relates to an instrument for the surgical treatment of an intervertebral disc by the anterior route, in particular by percutaneous nucleotomy, advantageously of use in the treatment by the coelioscopic surgical treatment of the lumbar disc situated between the fifth lumbar vertebra and the sacrum (commonly termed disc L5-S1).

The treatment of intervertebral discs has recently developed owing to, among other techniques, the techniques of percutaneous surgery which has in particular the advantage of being "non-invasive". Indeed, this surgery has created not only on the part of the patients but also on the part of hospital or medical protection authorities a very high interest. This interest is principally due to the very appreciable improvement in the post operational conditions and to a considerable reduction in the time spent in hospital. On the other hand, this surgery is relatively costly as concerns equipment and requires a more intense surgical specialization both in the operating theatre and of the specially trained surgeons.

The principle of percutaneous nucleotomy consists in puncturing the disc so as to lower the intradiscal pressure and possible withdrawing the degenerated discal contents without need of a truly surgical approach. Heretofore only a postero-lateral approach under radioscopic control was employed, the patient being placed in the ventral or possibly lateral decubitus position. The nucleus is removed either by means of a forceps (the most frequent case), or by means of a laser (technique at present under development) or with the use of a motorized system for fragmenting the disc and aspirating the debris.

The indications are mainly the nerve compressions by intraspinal discal protrusions or hernias. The sciaticas and non-excluded discal hernias are also indicated provided the patient is young and the posterior annulus is healthy.

Most often, it concerns the last three lumbar discs: L3-L4 and above all L4-L5 and L5-S1, the hernia of the latter two discs being responsible for most of the "common" discal sciaticas. Notwithstanding the fact that many technical points remain controversial (need for a discoscopy, manual or automated discectomy, etc.), there is a more or less general consensus as concerns the technique of a percutaneous approach of the lumbar discs; up to the present time all the authors consider that the puncturing of the disc must be effected by the postero-lateral route under radioscopic control. The penetration of the treatment device occurs at the postero-lateral angle of the disc, by avoiding the spinal nerve, which implies the use of local anaesthesia.

Surgeons generally acknowledge the interest of this operating technique owing to the relative ease of access it affords, in particular for the lumbar discs L3-L4 and L4-L5. On the other hand, approaching the disc L5-S1, the disc concerned in almost half the operations on lumbar discs, is more difficult owing to the much less superficial character of this spinal segment and to the necessity to pass round the iliac wing. This is why various specific artifices have been proposed for approaching the disc L5-S1: curved instrument, inclination of the spine etc. But there appears to be a relatively high rate of considerable technical difficulties or even failures. These difficulties moreover result in an increase in the duration of the intervention, of the irradiation of the patients and the impossibility of the use of instruments of large calibre.

An object of the invention is therefore to solve this problem by proposing a solution which is both simple and effective.

According to the invention, the surgical treatment instrument comprises a guide-needle, at least two rectilinear concentric telescopic tubes adapted to be mounted on the guide-needle, and an outer work tube concentric with the aforementioned tubes. The latter are slidable in this outer tube which is provided at its apical end adapted to penetrate the disc to be treated, with a means for separating the vertebrae adjacent this disc and maintaining this separation during the surgical treatment, while its proximal end is provided with a manual gripping knob.

Thus the instrument according to the invention is specially adapted for approaching the disc by the anterior route and no longer by the postero-lateral route. This instrument is essentially constituted by an assembly of concentric telescopic tubes, of which the outer work tube is provided with a means for separating the vertebrae, or the fifth lumbar vertebra and the sacrum if it concerns the treatment of the disc L5-S1. Owing to this separation, any untimely expulsion of the tube due to intersomatic hyperpressure is avoided. The maintenace of this separation during the intervention permits easily carrying out the intervention on the disc, in particular a nucleotomy, in an effective and rapid manner, without harming the anatomic environment of the patient.

In one embodiment of the invention, the means for separating and maintaining the vertebrae separated comprises an olive-shaped member which projects from the outer tube and is fixed coaxially to the latter at its apical end. This olive-shaped member has two symmetrical lateral flats connected to two symmetrical rounded bosses, the distance between the two flats being consequently less than the distance between the two tops of the bosses so that, by rotation of the outer tube through about 90° from its position in which the flats are parallel to the general plane of the disc to be treated, the subjacent and superjacent vertebral bodies can be separated and maintained in the separated position.

In another possible embodiment of the invention, the outer tube is double and is constituted by two concentric tubular elements axially slidable relative to each other, the gripping knob is provided on the proximal end of the outer tubular element, in the apical end of which is provided at least one opening, and the apical end of the interior element is provided with at least one resiliently flexible blade which projects outside said element in the free state, is retracted when the inner element is slidingly inserted in the outer element and projects from the latter through the corresponding opening so as to constitute said means for separating the vertebral bodies, when the outer element is in the desired angular position between the vertebral bodies.

In the various possible embodiments of the invention, the separating means are such that they oppose as little as possible the penetration of the tube into the body of the patient, then into the disc to be treated. These means are so arranged as to create a sufficient separation of the neighbouring vertebrae and maintain this separation with safety during the nucleotomy operation.

As compared with the other surgical techniques, namely discectomy with posterior instrumentation and laminectomy on L5, the advantages of percutaneous nucleotomy are essentially the following: short intervention time, small scars, mobility maintained without fusion, and absence of fibrosis.

Apart from the advantages mentioned hereinbefore of the anterior approach as compared with the postero-lateral approach of the disc, the anterior approach has the following advantages:

absence of hindrance by the iliac apex in the approach, improved decompression of the nerve roots since the surgeon has access to the most harmful fragments of the disc.

The invention will now be described with reference to the accompanying drawings which illustrate two embodiments thereof by way of non-limitative examples.

FIG. 1 is a longitudinal elevational view of a first embodiment of the surgical treatment instrument according to the invention, to a reduced scale.

FIG. 2 is an elevational view in the direction of arrow K of the manual control knob of the instrument of FIG. 1.

FIG. 3 is a partial longitudinal elevational view to a larger scale of the apical end of the instrument of FIGS. 1 and 2 equipped with an embodiment of the means for separating the vertebral bodies.

FIG. 4 is a partial top view of the apical end of the outer tube shown in FIG. 3.

FIGS. 6 and 7 are diagrammatic elevational views of the disc L5-S1, the neighbouring vertebral bodies and the two possible positions of the means for separating these vertebral bodies by rotation of the work tube through about 90°.

FIG. 8 is a perspective view, with a part broken away and to a small scale, of a second embodiment of the outer work tube of the instrument according to the invention, in which this tube is double and provided with a retractable device for separating the vertebrae.

FIG. 9 is a perspective view of the outer tube of FIG. 8.

FIG. 10 is a perspective view, with a part broken away, of the inner tube of FIG. 8.

Figure 5:
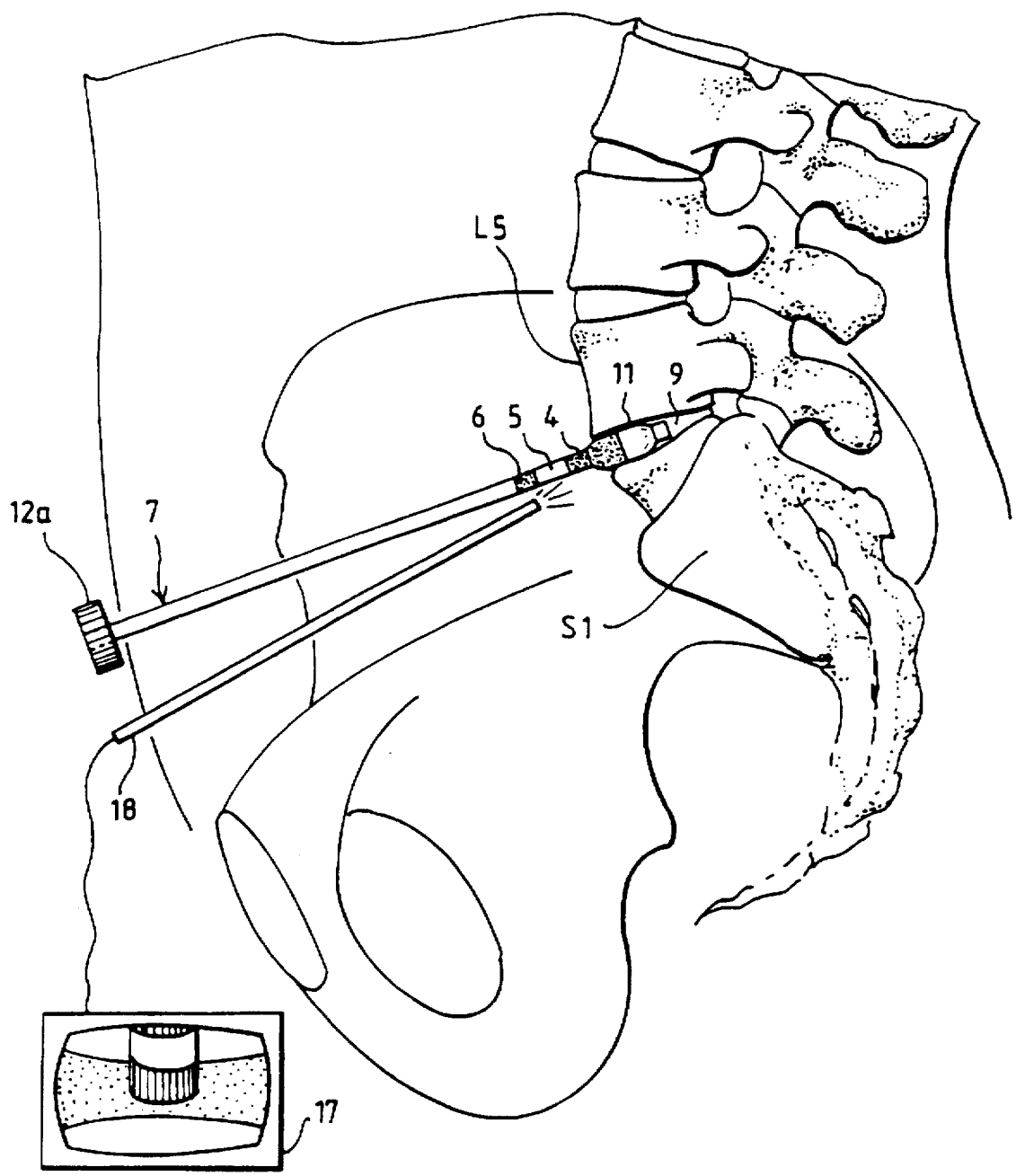
FIG. 5 is a diagrammatic elevational view of the principle of the approach of the disc L5-S1 by means of the instrument of FIGS. 1 to 4 and under laparoscopic control.

Coelioscopy is the technique for controlling the advance and the positioning of the nucleotomy device constituted by the instrument according to the invention. This technique is usual in visceral coelioscopic surgery, it being frequently employed in the small pelvis and the promontory. Heretofore it was practically unknown to orthopaedic surgeons, this technique being moreover capable of opening up for the latter other possibilities such as arthrodesis.

Recalled hereunder are the successive stages of the coelioscopic technique:

Effecting a pneumo-peritoneum by blowing carbon dioxide gas by means of an umbilical trocar.

Introducing optical equipment on the subumbilical midline.

Placing in position by incision of the left iliac fossa, outside the epigastric vessels, a troca permitting the introduction of the surgical equipment (dissecting forceps, scissors etc.).

Possibly by a symmetrical incision of the right side, placing in position an aspirator which also permits urging back the viscera.

Placing in position a median subpubic troca with the aid of an instrument for perforating the peritoneum. The optical equipment is then transfered in this troca and placed in front of the promontory. The location of the disc L5-S1 is achieved as in "open surgery" by upwardly urging back the epiploon, the transverse colon and the small intestine loops. The promontory is then easily recognized visually owing to its white colour, and by touch by the special elastic consistency of the intervertebral disc.

The surgical treatment instrument for percutaneous nucleotomy shown in FIGS. 1 to 7 will now be described.

This instrument comprises a guide-needle 1, at least two rectilinear concentric telescopic tubes and, in the illustrated embodiment, five telescopic tubes 2, 3, 4, 5, 6, increasing in diameter from the tube to the tube 6, adapted to be mounted on the guide needle 1 or troca, and lastly an outer work tube 7. The latter is also concentric with the troca 1 and the aforementioned tubes 2–6, so as to be slidable on the last tube 6.

The proximal end of the work tube 7 is provided with a manual gripping knob 8 the surface of which is advantageously knurled. Its apical end adapted to penetrate the disc to be treated, for example the disc 9 situated between L5 and S1 (FIGS. 5 to 7), is provided with a means for separating the vertebral bodies adjacent this disc and maintaining this separation during the surgical treatment. In the represented embodiment, this separating means comprises an olive-shaped member 11 projecting from the apical end of the work tube 7 to which it is coaxially fixed in that it is mounted on the latter by any suitable means, or is in one piece with this tube. The olive-shaped member 11 may also be made of the same material as the work tube 7 or of a different material. This olive-shaped member 11 has two lateral flats 12 which are symmetrical relative to the axis XX of the tube 7 and the instrument as a whole, connected to two rounded bosses 13 which are symmetrical to each other relative to the axis XX, and thus interposed between the flats 12. The flats 12 are connected to the bosses 13 by rounded edges 14. The distance d between the flats 12 is less than the distance $l_1$ between the tops 13a of the bosses 13. The latter have a substantially oval contour with a minor axis $l_1$ and a major axis $l_2$, the ratio $l_2/l_1$ being advantageously, but not limitatively, equal to 2.

The five telescopic tubes 2–6 have their apical ends tapered but not sharp and are advantageously graduated in the known manner, and the work tube 7 is provided with graduations 15, 16. The same is true of the trocar 1, all these graduations enabling the surgeon to check the progression into the disc of the successive tubes of the instrument by means of a television screen 17 connected to a coelioscopic probe 18 inserted in the peritoneal cavity (FIG. 5).

The work tube 7 has a length distinctly shorter than that of the other tubes 2–6 and the guide needle 1.

The trocar 1 must have a minimum of flexibility in the longitudinal direction and transverse direction so as to avoid the risk of fracture if the point comes into contact with a vertebral body, for example L5 or S1. The tubes 1–6 are preferably metallic since they must have their apical end tapered to facilitate their progression into the anatomic flesh and walls.

The intervention is carried out on the intervertebral disc, for example the disc 9 situated at position L5-S1, in the following manner:

1) The trocar 1 is inserted by the anterior route until its end penetrates the interior of the disc 9 (FIG. 5) its progression may be monitored by the surgeon on the television screen 7. The trocar 1 is adapted to act as a guide for the following telescopic tubes 2 to 6. First of all the first tube 2 is slipped on the guide trocar 1, then the tube 3 is slipped on the tube 2 and so on upto the tube 6. The tubes 2 to 6 fit exactly one inside the other and penetrate the annulus by urging back the peritoneal tissue, without sectioning any vascular-nerve element. Owing to their graduation, the surgeon can directly follow on the monitoring screen 17 the penetration of the tubes into the disc 9 without need to effect a radiographic checking. This penetration must be the same as that of the guide trocar 1.

2) The work tube 7 is then slipped on the tube 6. It is shorter than the preceding tubes 2 to 6 so as to permit more easily withdrawing the latter from the work tube 7. Indeed, as soon as the tube 7 is in position, the other tubes project from its proximal end beyond the control knob 8.

3) The surgeon inserts the apical end of the work tube 7 in the disc 9 in its angular position in which the two flats 12 are roughly parallel to the general plane of the disc 9 and therefore in the angular position of the tube 7 corresponding to the smallest separation between the vertebral bodies L5 and S1. This angular position may be checked by a corresponding reference mark provided diametrically on the knob (FIG. 2). When the reference mark 19 extends in a position in which it is substantially in the general plane of the intervertebral disc 9, the same is true of the flats 12 which together with the rounded edges 14 facilitate the progression and the correct positioning of the apical end of the tube 7 between the vertebrae. The bosses 13 therefore now extend substantially in the plane of the disc.

4) It now becomes possible for the surgeon to proceed to the separation of the vertebral bodies, for example L5 and S1. For this purpose, the surgeon turns through 90° the control knob 8 and consequently the tube 7 and the olive-shaped member 11. This rotation is facilitated by the rounded edges 14, and the two bosses or cams 13 are placed in a plane substantially perpendicular to the general plane of the disc 9. A second reference mark 21 arranged diametrically on the knob 8, perpendicular to the reference mark 19 enables the surgeon to check the position of the olive-shaped member 11 between the vertebral bodies L5 and S1: this reference mark 21 is practically perpendicular to the general plane of the disc 9 when the bosses 13 are themselves perpendicular to this plane. The distance between the vertebral bodies L5 and S1 then increases from d to $l_1$, and the latter remain maintained in this position owing to the appropriate geometry of the olive-shaped member 11. The latter in this way permits avoiding any untimely expulsion of the tube produced by the intersomatic hyperpressure which would oppose a nucleotomy of quality.

The guide-trocar 1 and the tubes 2 to 6 being withdrawn as indicated hereinbefore, the surgeon can evacuate the contents of the disc through the interior of the work tube 1 by any appropriate means such as a disc forceps or a curette.

It should be mentioned that the separation of the vertebral bodies must be effected in a sufficiently controlled manner. The rate of the separation depends of course on the speed of rotation of the work tube 7, but also on the ratio between the minor axis $l_1$ and the major axis $l_2$ of the oval section of the cam-olive-shaped member 11.

The placing in position of the instruments which appear to be necessary to the surgeon (arthroscope, laser, nucleotome, etc.) may be carried out in full safety through the work tube 7. This approach permits easily gained access, without special instruments, to the hernia contents.

The intervention is terminated by an abundant rinsing through the tube 7 which is then withdrawn and the haemostasis is checked. The coelioscopic instruments 18, 17 are also withdrawn. It has been found on a certain number of patients that the sciatic pain suffered by the latter completely disappeared after these interventions. From the postoperative point of view the patients were allowed to get up 24 hours after the operation and they returned home on the third postoperative day. Of course, these patients were not obliged to employ any external restraining means or practise a spinal re-education.

The anterior approach of the vertebral discs and particularly of the discs L5-S1 under coelioscopy is therefore relatively easy for surgeons trained in coelioscopic techniques. It permits solving some of the problems encountered in the carrying out of the percutaneous nucleotomy of the bodies L5-S1. The use of an adapted equipment increases the safety of this approach and permits envisaging an extension of its indications.

In the second embodiment of the instrument according to the invention shown in FIGS. 8 to 10, the outer tube 7 is replaced by a double tube constituted by two concentric tubular elements 22 and 23 axially slidable relative to each other. The outer tube 22 is provided at its proximal end with a control knob 8, while at least one preferably oblong opening 24 extending in the longitudinal direction of the tube is formed at its apical end. Provided between the opening 24 and the free end of the tube 22 is an inner annular shoulder 25 projecting into the tube 22.

The apical end of the inner tubular element 23 is provided with at least one resiliently flexible blade 26 which extends longitudinally and projects outside the tube 23 in its relaxed position. Preferably two spring blades 26 are thus positioned in a diametrically opposed manner on the tubular element 23 so as to cooperate with two rounded openings 24 of the element 22. The spring blade or blades 26 are so dimensioned as to be capable of passing through the corresponding opening or openings 24 and project laterally from the tube 22 with a sufficient resilient force when the tubular element 23 is slidably engaged in the tubular element 22 until the spring blades 26, which are first of all retracted, reach a position in facing relation to the openings 24 (position of FIG. 8) and become resiliently relaxed through the latter. In this position, the free end of the tubular element 23 comes into abutment with the shoulder 25 which blocks the tubular element 23 and the spring blade or blades 26 in this position. The assembly of the two tubular elements 22 and 23 with the openings 24 and the spring blades 26 constitute a retractable device for separating and maintaining the vertebrae. After the insertion of the guide-trocar 1 and the telescopic tubes 2 to 6, the surgeon slips the outer tube 22 on the tube 6 with the oblong openings 24 positioned in confronting relation to the vertebral bodies L5 and S1. Thereafter, he withdraws the tubes 2 to 6 and inserts in the tube 22 the inner tube 23 until the blades 26, retracted within 22, resiliently relax through the openings 24, beyond which they remain in a projecting position causing the separation of the neighbouring vertebral bodies. With the vertebral bodies separated in this way, the remainder of the intervention is effected in the same manner as previously described.

The advantage of the embodiment of FIGS. 8 to 10 resides in particular in the total uniformity of the diameter of the outer tube 22 in the course of its progression in the body of the patient, and therefore in the elimination of zones of greater resistance on the outer face of the tube. It will be noted that the blocking means 25 (which may be replaced by any other equivalent means) permits maintaining in complete safety the projecting position of the flexible blades 26.

Various alternative embodiments of the invention are possible. Thus, in particular the number of telescopic tubes (2–6) may vary, and the described devices for separating the vertebral bodies may be replaced by any other equivalent means. The olive-shaped member 11 may in particular be replaced by a single boss having a thickness double that of the bosses 13 and the knob 8 may be replaced by a T.

In its different possible embodiments, the invention has the advantage of permitting the use of an outer work tube whose diameter is distinctly greater than that of the tubes of the postero-lateral route employed heretofore which did not exceed 5 mm. Consequently it becomes possible to introduce in this outer tube a motorized system of extraction by aspiration having a diameter for example of 5 mm. which was not possible heretofore. Thus it is possible to employ an outer tube whose diameter maybe as much as the height of the disc.

We claim:

1. An instrument for the surgical treatment of an intervertebral disc by the anterior route comprising:

a guide needle;

at least two rectilinear concentric telescopic tubes adapted to be mountable on said guide-needle; and an outer work tube concentric with said telescopic tubes and within which said telescopic tubes are slidable, said outer tube having a first end adapted to penetrate the disc to be treated, said outer tube including means at said first end for separating the vertebral bodies adjacent the disc and for maintaining such separation during the surgical treatment.

2. The instrument according to claim 1 wherein said flats of said member are connected to the bosses by rounded edges.

3. The instrument according to claim 1, wherein said bosses have a substantially oval profile with a dimension along a major axis being approximately twice a dimension along a minor axis thereof.

4. The instrument according to claim 1 wherein said outer work tube has a length less than that of said telescopic tubes so as to facilitate the extraction of said telescopic tubes from the outer tube.

5. The instrument according to claim 1, wherein said outer tube includes a gripping knob at a second end opposite said first end, said knob configured for manual rotation of said instrument and including reference marks defined thereon for checking the angular position of the means for separating the vertebral bodies.

6. The instrument according to claim 1, wherein said means for separating and maintaining such separated position of the vertebral bodies includes a boss having a thickness sized to the desired separated position.

7. The instrument according to claim 1, wherein said outer tube has a diameter substantially equal to the height of the disc to be treated.

8. An instrument for the surgical treatment of an intervertebral disc by the anterior route comprising:

a guide needle;

at least two rectilinear concentric telescopic tubes adapted to be mountable on said guide-needle; and an outer work tube concentric with said telescopic tubes and within which said telescopic tubes are slidable, said outer tube having a first end adapted to penetrate the disc to be treated, said outer tube including means at said first end for separating the vertebral boding adjacent the disc and for maintaining such separation during the surgical treatment, wherein said outer tube includes:

two concentric tubular elements which are axially slidable relative to each other, one of said concentric elements including a gripping handle at a second end of the outer tube opposite said first end, said one of said concentric elements including at least one opening at an end opposite said handle, and the other of said concentric elements including at least one resiliently flexible blade which projects outside said elements in a free state and is retracted when said two tubular elements are concentrically disposed, aid blade being capable of projecting through said at least one opening.

9. The instrument according to claim 8, wherein said one of said concentric elements is provided with a stop including an inner annular shoulder in the interior thereof adjacent said opening and adapted to be contacted by said other concentric elements when said at least one blade projects through said at least one opening.

* * * * *